United States Patent [19]

Abbate et al.

[11] Patent Number: 5,463,896
[45] Date of Patent: Nov. 7, 1995

[54] STRESS TESTER

[75] Inventors: Agostino Abbate, Clifton Park; Julius Frankel, Rensselaer; Wilfried Scholz, Latham; Vito J. Colangelo, Troy; William J. Korman, Ballston Spa, all of N.Y.

[73] Assignee: The United States of America as represented by the Secretary of the Army, Washington, D.C.

[21] Appl. No.: 129,724

[22] Filed: Sep. 29, 1993

[51] Int. Cl.⁶ .............................. G01N 3/42; G01N 3/08
[52] U.S. Cl. .................... 73/81; 73/740; 364/508
[58] Field of Search .................... 73/81, 83, 84, 73/85, 740, 818, 781; 364/508

[56] References Cited

U.S. PATENT DOCUMENTS

| | | | |
|---|---|---|---|
| 4,283,955 | 8/1981 | Nagy et al. | 73/789 X |
| 4,383,450 | 5/1983 | Pringiers et al. | 73/81 X |
| 4,820,051 | 4/1989 | Yanagisawa et al. | 73/81 X |

*Primary Examiner*—Thomas P. Noland
*Attorney, Agent, or Firm*—Anthony T. Lane; Edward Goldberg; Michael C. Sachs

[57] ABSTRACT

A device is presented for measuring residual stresses in a solid component. The device includes a hardness measuring component which has an indenter for determining hardness at various locations. Stress ($\sigma$) data is obtained by converting the hardness measurements according to the formula $$a \cdot [\sqrt{4P_o^2 - 3P^2} - P],$$

where a is a constant in Kbar$^{-1}$ mm$^2$/kg, which depends on the type of material under test and also on the type of indentor used, where the pressure p is measured in kg/mm$^2$, and where the average pressure $p_o$ is the average value of mean pressure p along a radial cut line of the solid component specimen.

5 Claims, 2 Drawing Sheets

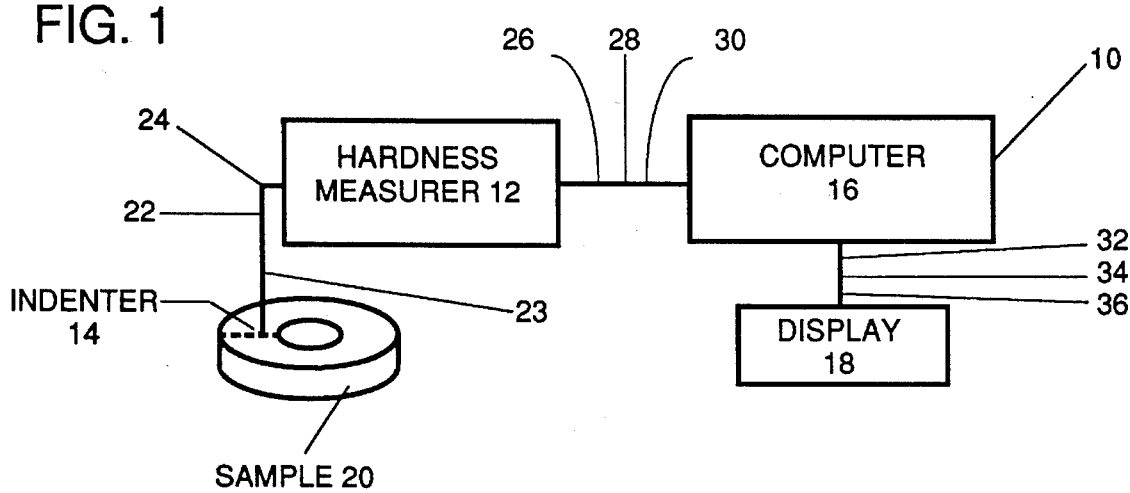
FIG. 1
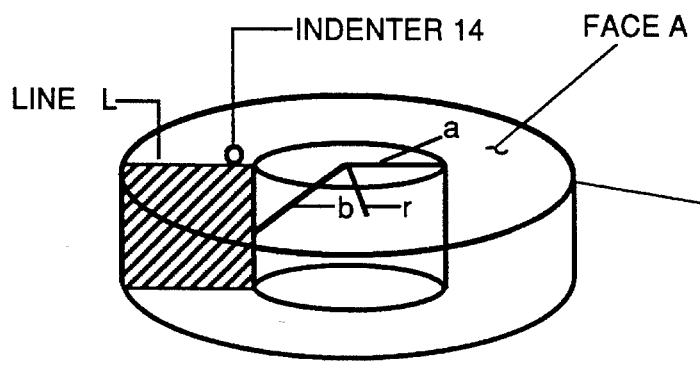
FIG. 2
FIG. 3
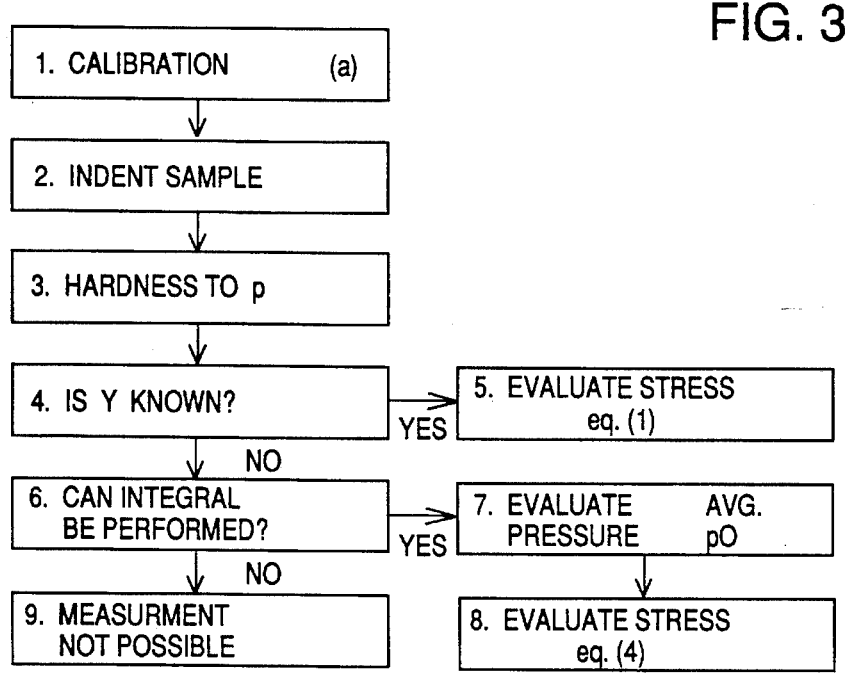

STRESS TESTER

GOVERNMENTAL INTEREST

The invention described herein may be manufactured, used, and licensed by or for the Government for governmental purposes without the payment to us of any royalties thereon.

FIELD OF THE INVENTION

The invention generally relates to a stress tester, and in particular the invention relates to a stress tester which has a hardness measurer and a computer which has a selectively designed software and which has a display unit.

BACKGROUND OF THE INVENTION

The performance of mechanical components which have to support either static or cyclic loads can be critically affected by residual or applied stresses, because these stresses affect their load limits and fatigue life. The presence and magnitude of these stresses can therefore be a concern in terms of safety, life or reliability of the component. On the other hand, there are instances in which the presence of residual stresses is desirable and thus they are induced by known means. In both cases, information on the magnitude of such stresses is required.

Prior art devices can obtain quantitative evidence of residual stresses by using x-ray lattice spacing determinations, or via ultrasonic bulk or surface wave velocities. For applied stresses, strain gauges are also used. All these techniques are difficult to execute, with usually stringent prerequisites and requirements.

The prior art machines have problems. X-ray machines usually limit the dimensions of the components to be tested. Ultrasonic bulk wave techniques require parallelism of two opposite surfaces, and work on the assumption that the measured stress is constant between those surfaces. The use of surface wave ultrasonic velocities require smooth surfaces and usually relatively large distances are needed for the required accuracy. Again, the stress must be constant along the path used to measure the surface wave velocity, since the wave should observe constant stresses over its travel. Often the components to be tested are such that the requirements for measurement are not met, i.e. the flat surface is not large enough for placement of an ultrasonic transducer, or a sufficiently large smooth surface is not available for sufficient resolution in the residual stress determination via surface waves, or two surfaces are not sufficiently parallel for the bulk wave determination.

SUMMARY OF THE INVENTION

According to the present invention, a stress tester is provided. This tester comprises a hardness measurer, which has an indenter, and includes a computer, which has software that is designed according to selective formulae for converting hardness data to stress data, and includes a display unit, which prints out the results and which saves the results in its memory.

By using the stress tester, which has a hardness measurer and a computer and a display unit, the abovementioned problems of the prior art x-ray machine and the prior art ultrasonic transducer and the prior art indentation device are avoided.

One object of the present invention is to avoid the problems of the prior art test devices, such as the limitation on sample size of the x-ray machine, and the limitation on sample surface size and smoothness of the ultrasonic transducer.

The foregoing and other objects, features and advantages will be apparent from the following description of the preferred embodiment of the invention as illustrated in the accompanying drawings.

BRIEF DESCRIPTION OF THE DRAWINGS

FIG. 1 is a block diagram of the stress tester according to the invention;

FIG. 2 is an enlarged perspective view of a portion of FIG. 1;

FIG. 3 is a schematic diagram of the method of operation of the stress tester according to the invention;

DESCRIPTION OF THE PREFERRED EMBODIMENT

Figure 4:
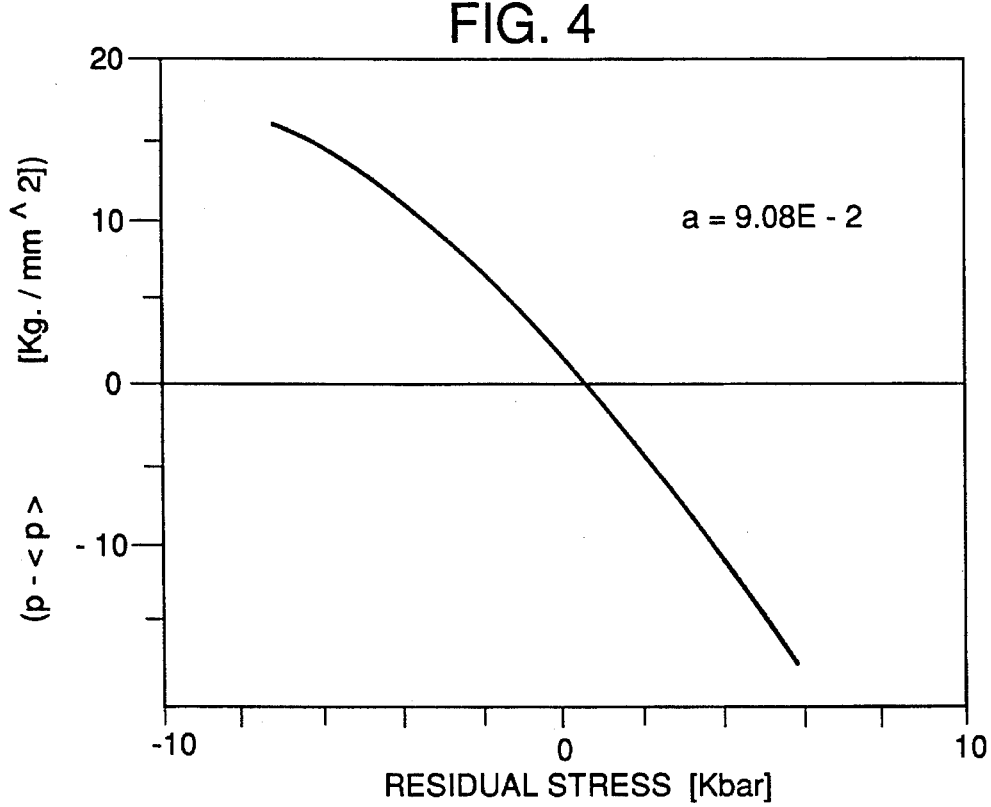
FIG. 4 is a calibration curve for a gun steel sample.

As shown in FIG. 1, a tester or device or apparatus or system 10 is provided. Tester 10 includes a hardness measurer or sensor 12 which has an indenter 14, and includes a computer or microprocessor 16 which has selectively designed software or firmware (not shown), and includes a readout or display unit 18. Tester 10 measures stress in a sample or a gun barrel specimen or a like specimen 20. Display 18 also includes a printer (not shown) and a memory (not shown). The software is designed according to selective formulae which convert surface hardness data to internal stress data, as described hereafter. Tester 10 can be a custom designed portable unit or it can be a non-portable unit which has standard parts.

As shown in FIG. 1, hardness measurer 12 has an input conduit or conductor 22, which connects to an indenter output terminal 23. Measurer 12 has an input terminal 24, which connects to conductor 22, and has an output terminal 26. Computer 16 has an input conductor 28, which connects to output terminal 26. Computer 16 has an input terminal 30, which connects to conductor 28, and has an output terminal 32. Display 18 has an input conductor 34, which connects to output terminal 32. Display 18 has an input terminal 36, which connects to conductor 34.

It is possible, by using an impinging test, to measure the stress distribution on a material. General hardness tests are: Rockwell, Vickers, Brinell and Meyer. The material or situation may dictate the preferred test to be used. Each of these measurements are related to each other empirically, either by means of a table or of an equation. Table I gives the related values for a range of hardness which is usually tested for gun steel. These values are taken from the publication, D. Tabor, The Hardness of Metals, Oxford University Press, London, England, 1951.

TABLE I

Hardness Conversion Table

| BRINELL 10-mm steel ball load 3,000 Kg. ($Kg/mm^2$) | VICKERS diamond pyramid hardness ($Kg/mm^2$) | ROCKWELL C 1500 Kg. load 120° diamond cone | MEYER 10-mm. Steel ball load 3,000 Kg. ($Kg/mm^2$) |
|---|---|---|---|
| 429 | 454 | 45 | 438 |
| 415 | 437 | 44 | 425 |
| 401 | 420 | 42 | 411 |
| 388 | 404 | 41 | 397 |
| 375 | 389 | 40 | 385 |
| 363 | 375 | 38 | 373 |
| 352 | 363 | 37 | 362 |
| 341 | 350 | 36 | 351 |
| 331 | 339 | 35 | 341 |

In particular, it is possible to obtain the Meyer Hardness Number (MHN) from any of the other tests. This number is equivalent to the average contact pressure (p) exerted by the ball at the indentation.

As shown in FIG. 2, to demonstrate the correlation, we use a specimen with a unidirectional residual stress σ on face A, of a hollow right circular cylinder. This stress is uniform as a function of depth. A relationship between the average contact pressure p of the indenter, the yield strength Y of the material and the stress σ can be obtained. An example of such a relation for a ball indenter is given by the equation (eq. 1) as follows:

$$\sigma = a \cdot [\sqrt{3 \cdot (12 \cdot Y^2 - p^2)} - p] \quad (1)$$

where the constant a depends on the type of material under test and also on the type of indenter used. For gun steel and for the stress measured in Kbar units, $a=9.08 \times 10^{-2}$ [kbar·mm²/kg], where the pressure p is measured in $kg/mm^2$.

Moreover, for any specimen where the applied or residual stresses and the specimen configuration are stable, we can say that the sum of forces on the entire plane generated by an imaginary cut through the entire specimen, have to be equal zero. For FIG. 2, a useful application of this condition is a cut generating a plane which contains the radius and is perpendicular to the surface A, and it is also perpendicular to the hoop stresses in the specimen. Since the stress is cylindrically symmetric and not a function of position along the axis of the cylinder, the forementioned condition for such surface results in:

$$\int_L \sigma_n(r) \cdot dr = 0 \quad (2)$$

where L represents the imaginary straight line going from the Inner Diameter (r=a) to the Outer Diameter (r=b). The subscript n on σ, refers to the fact that only the normal component of the stress to the surface is considered in the integral. In the case given by the example shown in FIG. 2, it is known that the stresses present in the cylinder are either normal (hoop) or parallel (radial) to the surface defined by line L. Therefore eq. 2 is applied only to the stress in the hoop direction of the ring in FIG. 2.

A consequence of both eq. 1 and 2 is that the average value of the mean pressure $p_o$ of a ball indenter along the line L is evaluated as:

$$p_o = 3 \cdot Y \quad (3)$$

In the case that either the direction of the stress σ is not known or the integral cannot be performed, eq. 1 can be sufficient to evaluate the stress, as long as also the yield strength Y of the material is known.

These considerations can be used to extract the value of the stress from the indentation tests. For each material to be characterized using the proposed measurement it is necessary to obtain the calibration constant a. The constant a can be used for subsequent measurements performed on samples of similar material.

Eq. 1 can be modified using eq. 3, resulting in:

$$\sigma = a \cdot (\sqrt{4p_o^2 - 3p^2} - p) \quad (4)$$

FIG. 3 shows the method steps necessary for the evaluation or determination of the stress using indentation measurements. Step 1 refers to the evaluation of the constant a to be used in the measurement. If the constant a is not known for the material in question, then calibration has to be performed on standard samples in order to obtain the constant. A detailed description of this operation can be found in the next section. Once the constant a is obtained, the actual measurement is initiated by performing indentation tests (Step 2). General hardness tests can be used for this purpose. Using empirical tables or equations, the mean pressure p can be evaluated (Step 3).

If the Yield Strength Y of the material is known (Step 4), then the stress can be evaluated using eq. 1 in Step 5.

If Y is not known, it must be defined if the possibility of performing the measurements along an imaginary cut L exists.

(Step 6). In the case that this possibility exists then the average pressure $p_o$ is evaluated (Step 7), using:

$$p_o = \frac{1}{N} \sum_{i=1}^{N} p_i \quad (5)$$

where N is the number of measurements performed along line L.

Once $p_o$ is obtained, in Step 8 the stress is evaluated using eq. 4.

The measurement cannot be performed if Y is not known or the equilibrium condition of eq. 3 cannot be used.

As shown in FIG. 4, the calibration curve was obtained for a gun steel sample. For each type of material to be characterized by this technique, the constant a must be obtained. In order to obtain the constant a, the indentation tests and stress measurements shall be performed on sample materials, which for the sake of this discussion we will address as standards. The hardness tests may be: Rockwell C or B, Meyer Hardness, Brinell Hardness, Vickers Hardness or other. Any commercially available Hardness Tester can be used. The stress can be measured ultrasonically, via X-rays or strain gauges. An X–Y plot is thus obtained of which the measured stress represents the abscissa (x-axis). FIG. 4 represents one such curve, obtained for gun steel. Three different data sets were obtained in order to verify results, even though one of such can be enough for calibration purposes. The value of the calibration constant a is obtained using Least Square Fitting of the experimental data. In particular, a is calculated as the value which minimizes the error function chi square, $X^2$:

$$\chi^2 = \sum_{i=1}^{N} \left[ \frac{p_i - f(\sigma_i)}{s_i} \right]^2 \quad (6)$$

where $p_i$, and $\sigma_i$ are the measured values of mean pressure and stress, respectively; $s_i$ is the standard deviation on the hardness measurement; and $f(\sigma_i)$ is either the inverse of eq. 1 or eq. 4. The constant a is related to the material composition and structure, therefore once obtained it can be used for different samples of the same material. The value of a obtained for Gun steel is shown in FIG. 4, this value was used in eq. 4 to plot the line in the figure. That line represents the calibration curve obtained. The value of $p_o$ was different for one of the three samples used for the calibration, even though the resulting constant a was the same.

Figure 5:
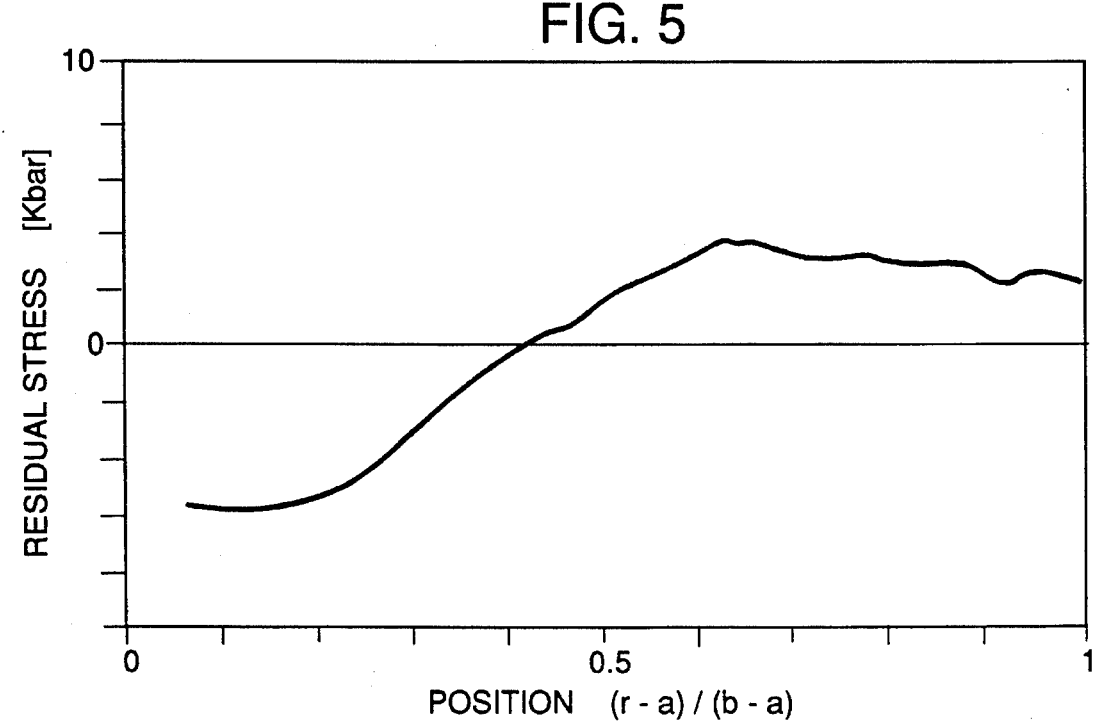
FIG. 5 is a curve of residual stress versus position on a cross section of a gun steel sample.

As shown in FIG. 5, the stress distribution of a gun steel sample was obtained. The stress distribution is on a cross section of a gun tube. The hardness tester used in the presented experiments was a Rockwell C tester, even though others could be used. The hardness of the sample was measured along a line L (FIG. 2). In order to reduce the error or standard deviation of the hardness data, three different lines of Rc measurements were performed and averaged. A PC computer was used to read the measured values of hardness, and to translate them to residual stress. Using the results presented in FIG. 4 (with $a=9.08\times10^{-2}$ [kbar·mm$^2$/kg]), the stress distribution was obtained. Results are shown in FIG. 5 as filled triangles. The residual stress was also measured using an ultrasonic technique to compare and verify results. The ultrasonic data is shown in FIG. 5 as a continuous line. From the comparison it can be inferred that the agreement is good, even though the standard deviation Of the results obtained using hardness data is larger. This is due to the intrinsic larger standard deviation of the hardness measurement itself, and it can be improved using better indentation or impingement tests. The ultrasonic technique is described in the publication, J. Frankel and W. Scholz, "Ultrasonic studies of stresses and plastic deformation in steel during tension and compression,"; review of progress in quantitative Nondestructive Evaluation, vol. 6B, pp. 1577–1584, 1987.

The advantages of tester 10 are indicated hereafter.

A) The problem of the prior art X-ray machine tester of a limitation on the size of a sample to be tested is avoided.

B) The problem of the prior art ultrasonic transducer tester of a limitation on surface size and surface smoothness of a sample to be tested is avoided.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. A stress tester comprising:

an indenter for applying a selective force on a specimen;

a hardness measurer connected to the indenter for measuring a hardness of the specimen;

a computer connected to the hardness measurer for receiving hardness data and having a selectively designed software for converting the hardness data to a corresponding stress data; and a readout connected to the computer for outputting the stress data; said selectively designed software designed to convert hardness data into stress data in accordance with the formula:

$$\sigma = a \cdot [\sqrt{3 \cdot (12 \cdot Y^2 - p^2)} - p]$$

where:
   a=a constant which depends on the type of material under test and also on the type of indenter used, and such constant for the stress ($\sigma$) is measured in Kbar units, and for gun steel $a=9.08\times10^{-2}$(kbar·mm$^2$/kg), and where the pressure p is measured in Kg/mm$^2$; and Y=the yield strength of the material, measured in Kg/mm$^2$.

2. The stress tester of claim 1, wherein the specimen has a hollow right circular cylinder shape, and wherein the selectively designed software is designed to also convert hardness data to stress data in accordance with the formula:

$$\sigma = a \cdot (\sqrt{4p_o^2 - 3p^2} - p)$$

where:
   a=a constant which depends on the type of material under test and also on the type of indentor used, and such constant for gun steel and for the stress $\sigma$ measured in kbar units, is $9.08\times10^{-2}$ [kbar·mm$^2$/kg], where the pressure p is measured in kg/mm$^2$, and where the average pressure $p_o$ is measured in kg/mm$^2$, and where the average pressure $p_o$ is the average value of mean pressure p along a radial cut line of the specimen.

3. The stress tester of claim 1, wherein the tester has a hardness measurer, and the tester has a computer, and said formula has the yield strength of the metal specimen under test, for determining the formula constant a.

4. The stress tester of claim 1, wherein the computer is a microprocessor unit.

5. The stress tester of claim 1, wherein the readout is a display unit, which shows and records residual stresses.

\* \* \* \* \*